(12) United States Patent
Kurachi et al.

(10) Patent No.: US 7,666,286 B2
(45) Date of Patent: Feb. 23, 2010

(54) GAS SENSOR

(75) Inventors: Hiroshi Kurachi, Aichi-Gun (JP); Yuichi Sasaki, Nagoya (JP); Takeya Miyashita, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 410 days.

(21) Appl. No.: 10/807,859

(22) Filed: Mar. 24, 2004

(65) Prior Publication Data

US 2004/0188251 A1 Sep. 30, 2004

(30) Foreign Application Priority Data

Mar. 31, 2003 (JP) .............................. 2003-096625
Mar. 15, 2004 (JP) .............................. 2004-072027

(51) Int. Cl.
*G01N 27/26* (2006.01)
*G01N 7/00* (2006.01)

(52) U.S. Cl. ........................ 204/408; 204/424; 204/425; 204/426; 204/427; 205/783.5; 73/23.31; 73/23.32

(58) Field of Classification Search ......... 204/424–429; 205/783.5–785; 73/23.31–23.32
See application file for complete search history.

(56) References Cited

U.S. PATENT DOCUMENTS

| | | | | |
|---|---|---|---|---|
| 5,288,389 | A | * | 2/1994 | Yamada et al. ............... 204/425 |
| 5,763,763 | A | | 6/1998 | Kato et al. ................... 205/781 |
| 5,948,963 | A | | 9/1999 | Kato et al. |
| 5,976,335 | A | * | 11/1999 | Kato et al. ................... 204/425 |
| 6,284,112 | B1 | | 9/2001 | Kato et al. ................... 204/425 |
| 6,287,439 | B1 | | 9/2001 | Kato et al. |
| 6,355,152 | B1 | | 3/2002 | Kato et al. |
| 6,660,142 | B2 | * | 12/2003 | Sugiyama et al. ........... 204/408 |
| 6,770,181 | B2 | * | 8/2004 | Kato et al. ................... 204/425 |
| 2002/0060151 | A1 | | 5/2002 | Kato et al. ................... 204/425 |

FOREIGN PATENT DOCUMENTS

| | | |
|---|---|---|
| EP | 0 678 740 A1 | 10/1995 |
| EP | 0937980 | 8/1999 |
| JP | 8-271476 | 10/1996 |
| JP | 9-113484 | 5/1997 |
| JP | 10-318979 | 12/1998 |
| JP | 10-318980 | 12/1998 |
| JP | 11-166913 | 6/1999 |
| JP | 11-237362 | 8/1999 |
| JP | 2000-028576 | 1/2000 |
| JP | 2000-180410 | 6/2000 |
| JP | 2000-214130 | 8/2000 |
| JP | 2001-013106 | 1/2001 |

* cited by examiner

*Primary Examiner*—Jennifer K Michener
*Assistant Examiner*—Matthew J Merkling
(74) *Attorney, Agent, or Firm*—Burr & Brown

(57) ABSTRACT

A gas sensor includes a first space for a measurement gas from a gas-introducing hole via a first diffusion rate-determining section, a main pumping means for controlling a partial pressure of oxygen in the measurement gas introduced into the first space to have a predetermined value, a second space for the measurement gas from the first space via a second diffusion rate-determining section, and a measuring pumping means for reducing or decomposing a NOx component in the measurement gas introduced from the second space via a third diffusion rate-determining section so that oxygen produced thereby is pumped out to detect a current generated by pumping out the oxygen. A ratio (Wc/We) between a width (We) of an end of a sensor element and a width (Wc) of the gas-introducing hole is not less than 0.3 and less than 0.7.

9 Claims, 17 Drawing Sheets

(Wc/We)=50%

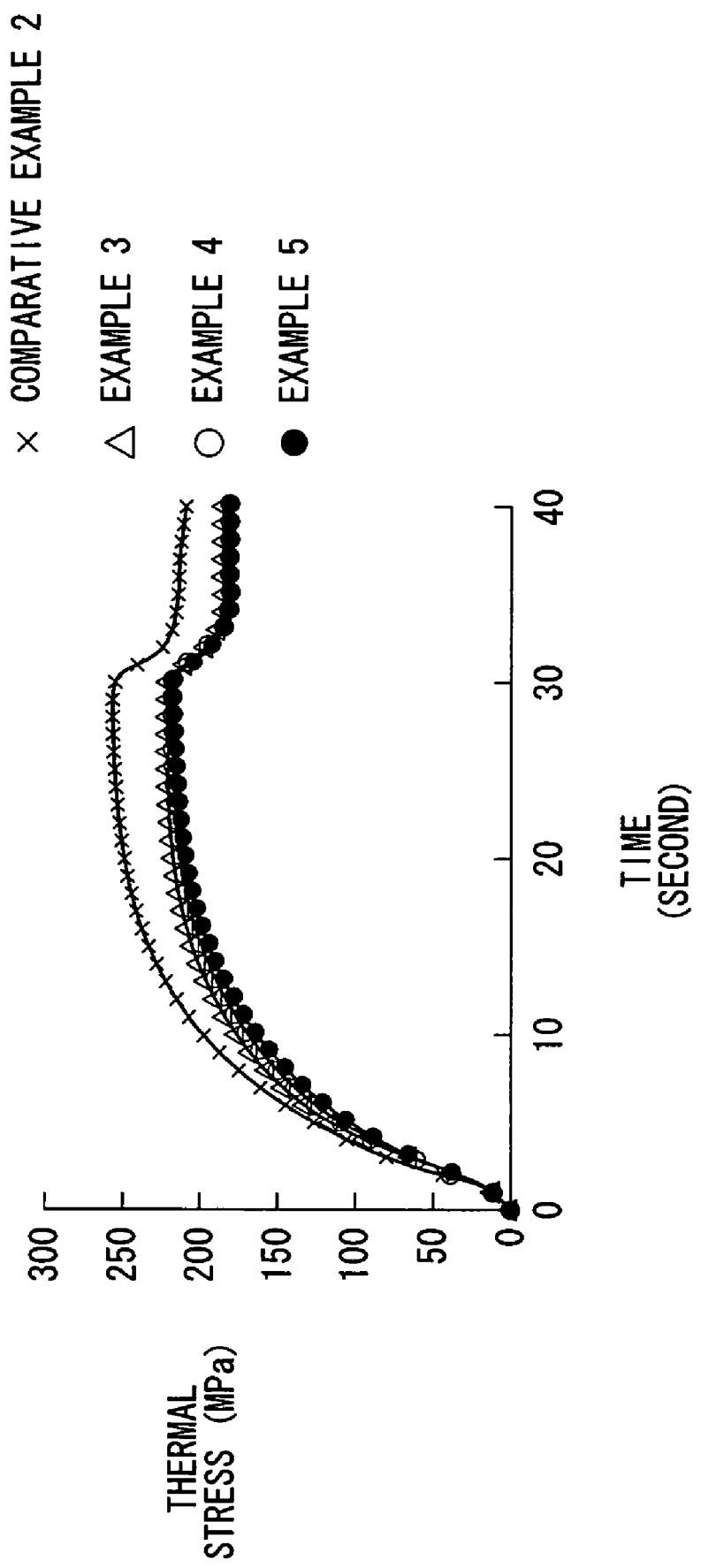

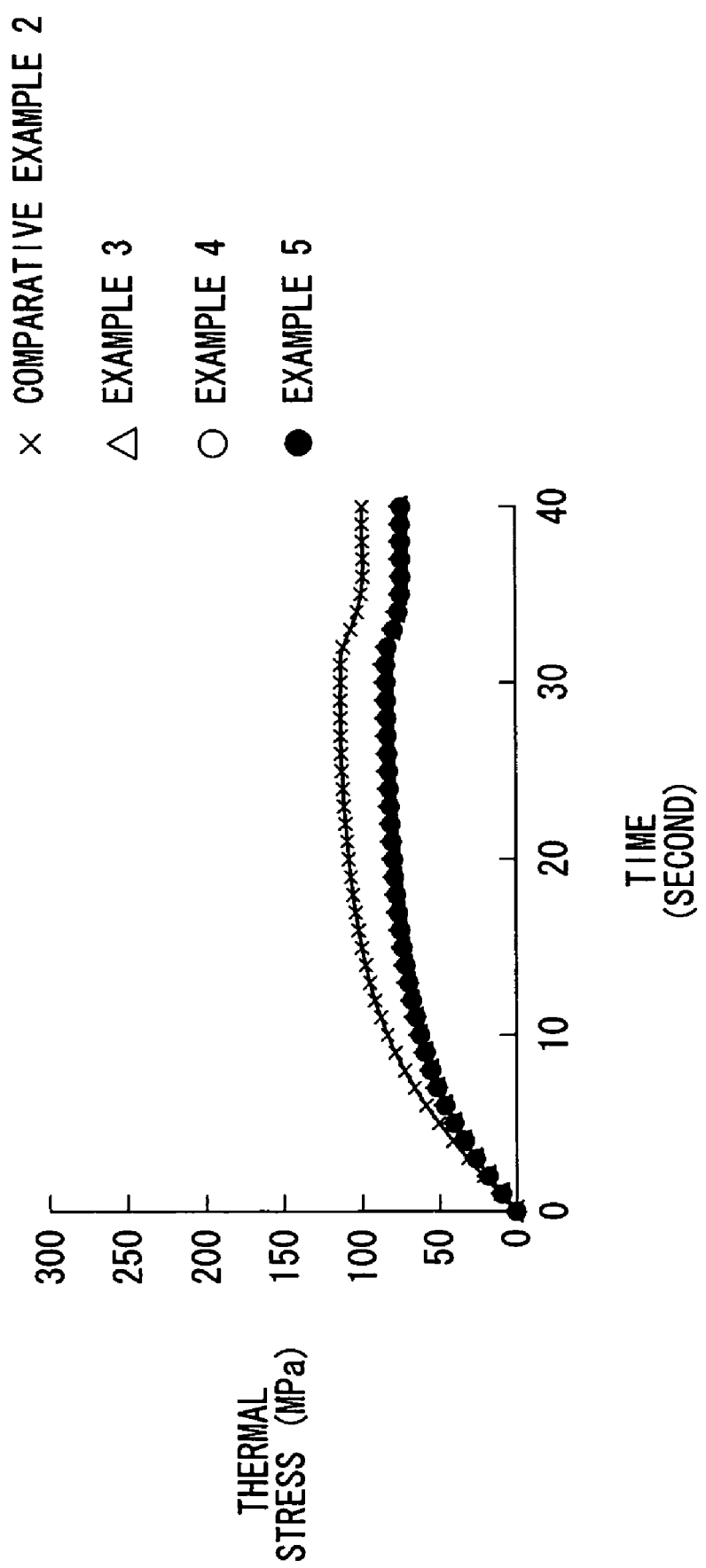

GAS SENSOR

This application claims the benefit of Japanese Application 2003-096625, filed Mar. 31, 2003, and Application 2004-072027, filed Mar. 15, 2004, the entireties of which are incorporated herein by reference.

BACKGROUND OF THE INVENTION

1. Field of the Invention

The present invention relates to a gas sensor. In particular, the present invention relates to a gas sensor which is preferably usable, for example, to measure NOx contained in the atmospheric air and the exhaust gas discharged from vehicles or automobiles.

2. Description of the Related Art

A method of measuring NOx contained in the measurement gas such as the combustion gas is disclosed, for example, in Japanese Laid-Open Patent Publication No. 8-271476. In this method, a first space communicating with the external space and a second space communicating with the first space are provided, and the oxygen concentration is adjusted by using a pumping cell provided in the first space, NOx is reduced or decomposed in the second space, and the NOx concentration is measured from the pumping current flowing through a measuring pumping cell in the second space.

On the other hand, Japanese Laid-Open Patent Publication No. 9-113484 discloses a gas sensor in which an auxiliary pumping cell is provided in a second space so that the oxygen concentration in the second space is controlled to be constant even when the oxygen concentration is suddenly changed.

Further, as a gas sensor disclosed in Japanese Laid-Open Patent Publication No. 11-237362, the measurement accuracy is improved for a detecting electrode by avoiding the influence of pulsation of the exhaust pressure generated in the measurement gas.

SUMMARY OF THE INVENTION

An object of the present invention is to provide a gas sensor in which the stress generated in a sensor element is reduced by decreasing the occurrence of cracks or the like by adjusting the space in the sensor element in the gas sensor as described above, making it possible to improve the reliability.

According to the present invention, there is provided a gas sensor comprising a sensor element having a gas-introducing hole close to an end of the sensor element; the sensor element including a first space for introducing a measurement gas thereinto from the gas-introducing hole via a first diffusion rate-determining section, a main pumping means for controlling a partial pressure of oxygen contained in the measurement gas introduced into the first space to be substantially constant, a second space for introducing the measurement gas thereinto from the first space via a second diffusion rate-determining section, and an electric signal-generating converting means for reducing or decomposing a NOx component contained in the measurement gas introduced from the second space via a third diffusion rate-determining section to generate an electric signal corresponding to a an amount of oxygen produced thereby so that a concentration of NOx existing in the measurement gas is determined from the electric signal, wherein $$0.3 \leq (Wc/We) < 0.7$$

wherein We represents a lateral width of the end of the sensor element, and Wc represents a lateral width of the gas-introducing hole.

The electric signal-generating converting means may be a measuring pumping means which reduces or decomposes the NOx component contained in the measurement gas introduced from the second space via the third diffusion rate-determining section, which pumps out oxygen produced thereby, and which detects a current generated by pumping out the oxygen.

Alternatively, the electric signal-generating converting means may be a detecting means which reduces or decomposes the NOx component contained in the measurement gas introduced from the second space via the third diffusion rate-determining section and which detects an electromotive force corresponding to a difference between an amount of oxygen produced by the reduction or decomposition and an amount of oxygen contained in a reference gas.

In general, as for the gas sensor, the sensor element is maintained at a predetermined temperature by using, for example, a heater in order to improve the detection accuracy. When the measurement gas having an arbitrary temperature is introduced in this state, thermal stress, which is caused by the temperature change, is generated in the sensor element. In particular, the space is formed in the vicinity of the gas-introducing hole, and hence a structure is formed, in which the mechanical strength is low and the stress is apt to be concentrated.

Therefore, for example, when sudden temperature change takes place, crack may appear around a base point or start point at which the stress is concentrated.

However, in the present invention, the ratio (Wc/We) between the lateral width We of the end of the sensor element and the lateral width Wc of the gas-introducing hole is not less than 0.3 and less than 0.7. Accordingly, the mechanical strength is increased in the vicinity of the gas-introducing hole, and the generated thermal stress is reduced as well.

As a result, it is possible to reduce the stress generated in the sensor element, and it is possible to decrease the appearance of the crack or the like in the sensor element. This results in the improvement in reliability of the gas sensor.

If the ratio (Wc/We) is too large, the mechanical strength may be undesirably lowered in the vicinity of the gas-introducing hole and the crack tends to appear. On the other hand, if the ratio (Wc/We) is too small, the gas sensor does not function properly.

In the gas sensor constructed as described above, it is preferable that the sensor element further includes a heater for maintaining at least the first space and the second space at a predetermined temperature, and $$0.2 < (La/We) < 0.5$$

wherein La represents a distance from a projected position of an end of the heater on an upper surface of the sensor element to the end of the sensor element.

Accordingly, the heat generated by the heater is hardly transmitted to the portion in the vicinity of the gas-introducing hole. The sudden temperature change, which would be otherwise caused by the introduction of the measurement gas, scarcely arises. As a result, it is possible to further reduce the stress generated in the sensor element, and it is possible to further improve the reliability of the gas sensor.

When the partial pressure of oxygen of the measurement gas introduced into the first space is controlled to be substantially constants the efficiency is proportionally improved as the volume of the first space is increased, in which the partial pressure of oxygen of the measurement gas having a large volume can be controlled to be substantially constant.

In view of the above, firstly, the width of the first space may be increased in order to increase the volume of the first space. However, in such an arrangement, the mechanical strength of the side wall for sectioning the first space may be undesirably lowered and crack may appear in the side wall, if the lateral width of the sensor element is limited in order to miniaturize the gas sensor.

Alternately, the length of the first space may be increased. However, if the starting end of the first space is disposed close to the gas-introducing hole, the mechanical strength is undesirably lowered in the vicinity of the gas-introducing hole, and it is impossible to expect the decrease of stress in the vicinity of the gas-introducing hole.

Therefore, it is preferable that the projected position of the end of the heater on the upper surface of the sensor element is approximately coincident with a projected position of a starting end of the first space on the upper surface of the sensor element.

Accordingly, it is possible to realize the reduction of the stress in the vicinity of the gas-introducing hole, and it is possible to realize the expansion of the volume of the first space as well.

In the gas sensor constructed as described above, it is also preferable that each of the first diffusion rate-determining section and the second diffusion rate-determining section is defined by a slit provided in the sensor element.

It is also preferable that the sensor element further includes a fourth diffusion rate-determining section disposed between the gas-introducing hole and the first diffusion rate-determining section; a space between the gas-introducing hole and the fourth diffusion rate-determining section functions as a clogging-preventive space; and another space between the fourth diffusion rate-determining section and the first diffusion rate-determining section functions as a buffering space.

Accordingly, for example, when the oxygen suddenly enters the sensor element via the gas-introducing hole on account of the pulsation of the exhaust pressure, the oxygen suddenly introduced does not enter the first space directly. However, the oxygen enters the buffering space before the first space. In other words, the sudden change of the oxygen concentration, which is brought about by the pulsation of the exhaust pressure, is counteracted in the buffering space. Thus, the influence of the pulsation of the exhaust pressure against the first space is substantially negligible.

Further, by the clogging-preventive space, it is possible to avoid clogging in the vicinity of the inlet of the buffering space, which would be otherwise caused by particulates (for example, soot and oil combustion waste) existing in the measurement gas.

The fourth diffusion rate-determining section may be constructed by a slit provided in the sensor element.

Further, it is preferable that a lateral width of the clogging-preventive space, a lateral width of the buffering space, a lateral width of the slit for constructing the first diffusion rate-determining section, and a lateral width of the slit for constructing the fourth diffusion rate-determining section are substantially identical with each other. Of course, the lateral width of the gas-introducing hole may be substantially identical with the lateral width of the clogging-preventive space.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 14 shows changes of the thermal stress at Point P1 as time passes in Comparative Example 2 and Examples 3 to 5;

FIG. 15 shows changes of the thermal stress at Point P2 as time passes in Comparative Example 2 and Examples 3 to 5;

DESCRIPTION OF THE PREFERRED EMBODIMENTS

Illustrative embodiments of the gas sensor according to the present invention will be explained below with reference to FIGS. 1 to 17.

Figure 1:
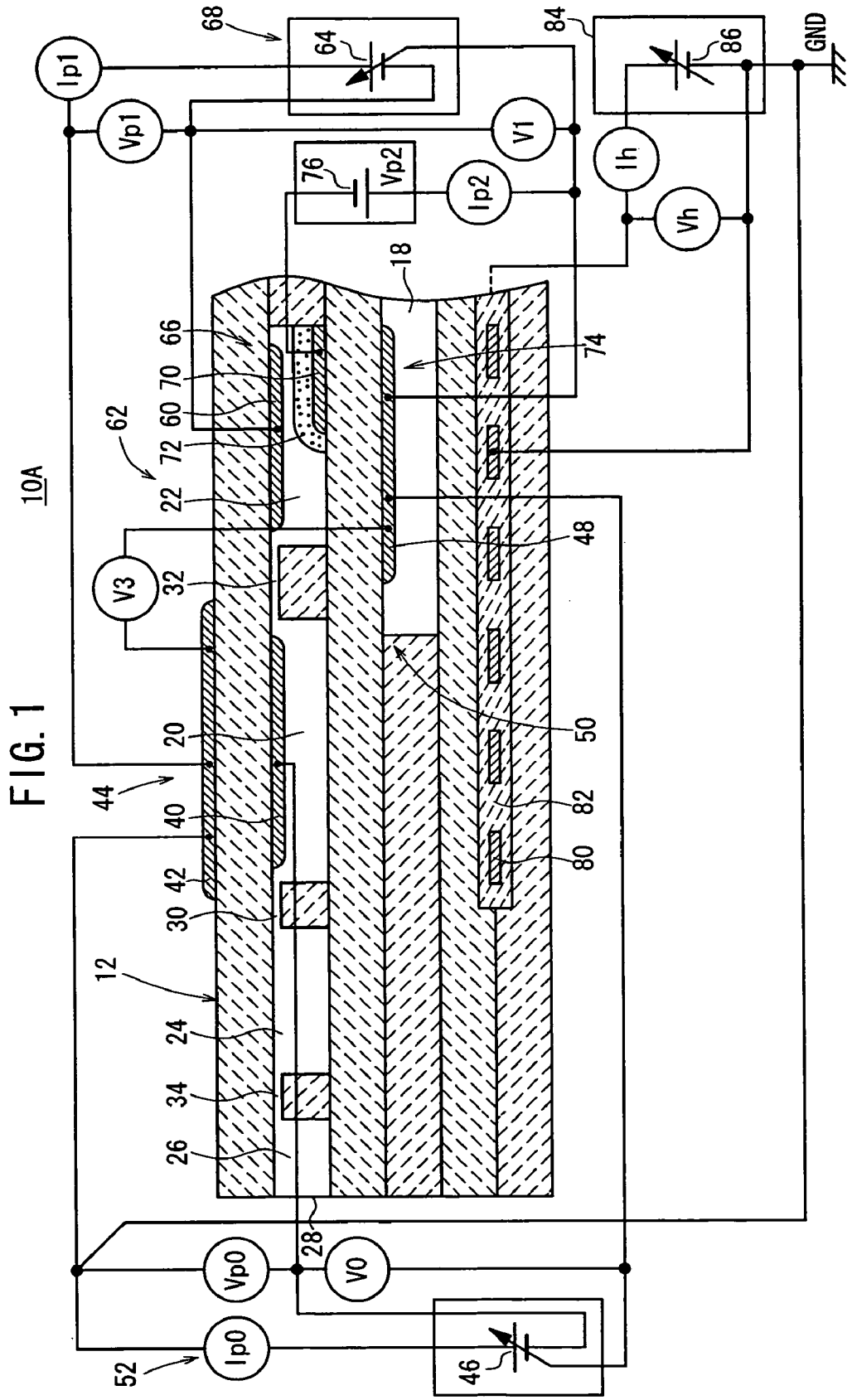
FIG. 1 shows a cross-sectional arrangement illustrating a gas sensor according to a first embodiment.

As shown in FIG. 1, a gas sensor 10A according to a first embodiment comprises a sensor element 12 constructed by stacking, for example, six solid electrolyte layers each of which is composed of a ceramics based on the use of an oxygen ion-conductive solid electrolyte such as $ZrO_2$.

The sensor element 12 has a slit-shaped gas-introducing hole 28. The gas-introducing hole 28 is disposed at an end of the sensor element 12 and has a horizontal length longer than a vertical length. The gas-introducing hole 28 has a predetermined opening area.

The sensor element 12 has a first space 20 into which a measurement gas is introduced from the gas-introducing hole 28 via a first diffusion rate-determining section 30, a second space 22 into which the measurement gas is introduced from the first space 20 via a second diffusion rate-determining section 32, and a space (reference gas-introducing space 18) into which a reference gas, for example, atmospheric air is introduced to serve as a reference for measuring NOx.

The sensor element 12 includes a main pumping means 44 which controls the partial pressure of oxygen contained in the measurement gas introduced into the first space 20 to be substantially constant, a first detecting means 50 which detects the partial pressure of oxygen in the first space 20, an auxiliary pumping means 62 which controls the partial pressure of oxygen contained in the measurement gas introduced into the second space 22 to have a predetermined value, a second detecting means 66 which detects the partial pressure of oxygen in the second space 22, and a measuring pumping means 74 which reduces or decomposes the NOx component contained in the measurement gas introduced from the second space 22 via a third diffusion rate-determining section 72, which pumps out oxygen produced thereby, and which detects the current generated by pumping out the oxygen. In this case, the reduction or decomposition of the NOx component may be the reduction by utilizing the catalytic action while using a NOx-reducing catalyst electrode for a detecting electrode 70, for example, or the decomposition by the voltage applied to the measuring pumping means 74.

The gas sensor 10A is operated such that the concentration of NOx in the measurement gas is determined from the value of the current detected by the measuring pumping means 74.

The sensor element 12 further includes a fourth diffusion rate-determining section 34 that is arranged between the gas-introducing hole 28 and the first diffusion rate-determining section 30. The space between the gas-introducing hole 28 and the fourth diffusion rate-determining section 34 functions as a clogging-preventive space 26. The space between the fourth diffusion rate-determining section 34 and the first diffusion rate-determining section 30 functions as a buffering space 24.

In this arrangement, the first diffusion rate-determining section 30, the second diffusion rate-determining section 32, and the fourth diffusion rate-determining section 34 give predetermined diffusion resistances to the measurement gas to be introduced into the buffering space 24, the first space 20, and the second space 22, respectively. Each of the first diffusion rate-determining section 30, the second diffusion rate-determining section 32, and the fourth diffusion rate-determining section 34 is slit-shaped having a horizontal length longer than a vertical length and has an opening area narrower than the opening area of the gas-introducing hole 28.

The third diffusion rate-determining section 72 in the second space 22 comprises, for example, a porous alumina film which covers the detecting electrode 70 of the measuring pumping means 74 as described later on.

A porous member, which is composed of $ZrO_2$ or the like, may fill the slit of the second diffusion rate-determining section 32 so that the diffusion resistance of the second diffusion rate-determining section 32 is larger than the diffusion resistance of the first diffusion rate-determining section 30. It is preferable that the diffusion resistance of the second diffusion rate-determining section 32 is larger than the diffusion resistance of the first diffusion rate-determining section 30. However, there is no problem even if the diffusion resistance of the second diffusion rate-determining section 32 is smaller than the diffusion resistance of the first diffusion rate-determining section 30.

The main pumping means 44 includes an inner pumping electrode 40 which comprises a porous cermet electrode or the like formed in the first space 20, an outer pumping electrode 42 which comprises a porous cermet electrode or the like formed outside the first space 20, and the solid electrolyte layer which is interposed between both of the electrodes 40, 42.

A desired control voltage (pumping voltage) Vp0 is applied between the inner pumping electrode 40 and the outer pumping electrode 42 of the main pumping means 44 by an external variable power source 46 to flow a pumping current Ip0 in the positive or negative direction between the outer pumping electrode 42 and the inner pumping electrode 40. Accordingly, oxygen can be pumped out from the first space 20 to the outside, or oxygen can be pumped into the first space 20 from the outside.

The first detecting means 50 includes a reference electrode 48 which is formed in the reference gas-introducing space 18, the inner pumping electrode 40 which is formed in the first space 20, and the solid electrolyte layer which is interposed between the electrodes 48, 40.

The first detecting means 50 is capable of detecting the partial pressure of oxygen in the first space 20 by an electromotive force generated between the inner pumping electrode 40 and the reference electrode 48 on the basis of the difference in oxygen concentration between the atmosphere in the first space 20 and the reference gas (atmospheric air) in the reference gas-introducing space 18.

The detected value of the partial pressure of oxygen is used to perform feedback control of the variable power source 46. Specifically, the pumping action of the main pumping means 44 is controlled by a feedback control system 52 for the main pump so that the partial pressure of oxygen in the first space 20 has a predetermined value which is sufficiently low to successfully control the partial pressure of oxygen in the second space 22.

The feedback control system 52 performs feedback control of the pumping voltage Vp0 between the outer pumping electrode 42 and the inner pumping electrode 40 so that the difference (detection voltage V0) between the electric potential of the inner pumping electrode 40 and the electric potential of the reference electrode 48 is at a predetermined voltage level.

Therefore, the main pumping means 44 pumps out or pumps in the oxygen contained in the measurement gas introduced into the first space 20 in an amount corresponding to the level of the pumping voltage Vp0. The series of operation as described above is repeated, and thus the feedback control is performed on the oxygen concentration in the first space 20 to have a predetermined level.

The auxiliary pumping means 62 includes an auxiliary pumping electrode 60 which is composed of, for example, a porous cermet electrode formed in the second space 22, the outer pumping electrode 42 which is formed outside the first space 20, and the solid electrolyte layer which is interposed between both electrodes 60, 42.

A desired auxiliary control voltage Vp1 is applied between the outer pumping electrode 42 and the auxiliary pumping electrode 60 of the auxiliary pumping means 62 by an external auxiliary variable power source 64. Accordingly, the oxygen is pumped out from the second space 22 to the outside, or the oxygen is pumped in from the outside into the second space 22.

The second detecting means 66 includes the reference electrode 48 which is formed in the reference gas-introducing space 18, the auxiliary pumping electrode 60 which is formed in the second space 22, and the solid. electrolyte layer which is interposed between both electrodes 48, 60.

The second detecting means 66 is capable of detecting the partial pressure of oxygen in the second space 22 by an electromotive force generated between the auxiliary pumping electrode 60 and the reference electrode 48 on the basis of the difference in oxygen concentration between the atmosphere in the second space 22 and the reference gas (atmospheric air) in the reference gas-introducing space 18.

The detected value of the partial pressure of oxygen is used to perform the feedback control of the auxiliary variable power source 64. Specifically, the pumping action of the auxiliary pumping means 62 is controlled by an auxiliary feedback control system 68 so that the partial pressure of oxygen in the second space 22 has a value of the partial pressure of oxygen which does not affect the measurement of the amount of the objective component in a situation in which the influence of oxygen is excluded for the measurement gas component (NOx).

The auxiliary feedback control system 68 performs the feedback control of the voltage (auxiliary control voltage) Vp1 between the outer pumping electrode 42 and the auxiliary pumping electrode 60 so that the difference (auxiliary detection voltage V1) between the electric potential of the auxiliary pumping electrode 60 and the electric potential of the reference electrode 48 is at a predetermined voltage level.

Therefore, the auxiliary pumping means 62 pumps out or pumps in the oxygen contained in the measurement gas introduced into the second space 22 in an amount corresponding to the level of the auxiliary control voltage Vp1. The series of operation as described above is repeated, and thus the oxygen concentration in the second space 22 is feedback-controlled to be a predetermined level.

In this arrangement, owing to the action of the main pumping means 44 in the first space 20, the change of the amount of oxygen to be introduced into the second space 22 is greatly reduced as compared with the change in the measurement gas. Therefore, the partial pressure of oxygen in the second space 22 is accurately maintained to be constant.

The measuring pumping means 74 includes the detecting electrode 70 which is composed of, for example, a porous cermet electrode covered with the third diffusion rate-determining section 72, the reference electrode 48 which is formed in the reference gas-introducing space 18, and the solid electrolyte layer which is interposed between the electrodes 70, 48.

The detecting electrode 70 is composed of a porous cermet which comprises an alloy of Rh and Pt as metals capable of reducing NOx as the measurement gas component, and zirconia as ceramics. Accordingly, the detecting electrode 70 functions as a NOx-reducing catalyst for reducing NOx existing in the second space 22. Further, when a constant voltage Vp2 is applied by a DC power source (constant voltage power source) 76 between the detecting electrode 70 and the reference electrode 48, the oxygen contained in the second space 22 can be pumped out to the reference gas-introducing space 18. The pumping current Ip2, which flows in accordance with the pumping action of the measuring pumping means 74, is detected by an ammeter.

The constant voltage power source 76 is capable of applying the voltage having a magnitude to give the limiting current with respect to the pumping of oxygen produced during the decomposition effected by the measuring pumping means 74 under the inflow of NOx restricted by the third diffusion rate-determining section 72.

The sensor element 12 further includes a heater 80 which is disposed at a lower portion thereof and which generates the heat in accordance with the supply of electric power from the outside. The heater 80 is provided in order to enhance the conductivity of oxygen ion. A ceramic layer 82 composed of alumina or the like is formed to cover upper and lower surfaces of the heater 80 in order to obtain the electric insulation with respect to the sensor element 12.

As shown in FIG. 1, the heater 80 is arranged over an entire area ranging from the first space 20 to the second space 22. Further, at least the first space 20 and the second space 22 are heated to a predetermined temperature respectively in accordance with the control effected by a heater output controller 84 connected to the heater 80. Simultaneously, the main pumping means 44, the first detecting means 50, the auxiliary pumping means 62, the second detecting means 66, and the measuring pumping means 74 are also heated to and maintained at the predetermined temperature. In this arrangement, the positive lead wire of the heater 80 is connected to a heater power source 86 via the heater output controller 84, and the negative lead wire of the heater 80 is grounded (GND).

The sensor element 12 is constructed such that the outer pumping electrode 42 of the main pumping means 44 is connected to the positive lead wire of the heater 80.

Next, the operation of the gas sensor 10A will be explained. First, the end of the sensor element 12 is arranged in the external space (for example, in the exhaust tube). Accordingly, the measurement gas, which flows through the exhaust tube or the like, is introduced into the first space 20 via the gas-introducing hole 28, the clogging-preventive space 26, the fourth diffusion rate-determining section 34, the buffering space 24, and the first diffusion rate-determining section 30.

The measurement gas, which has been introduced into the first space 20, is controlled so that the partial pressure of oxygen thereof has a predetermined value, for example, $10^{-7}$ atm in accordance with the pumping action for oxygen caused by the predetermined pumping voltage Vp0 applied between the outer pumping electrode 42 and the inner pumping electrode 40 of the main pumping means 44. This control is made by the feedback control system 52.

The first diffusion rate-determining section 30 functions to reduce the current flowing through the main pumping means 44 by limiting the amount of oxygen contained in the measurement gas to diffuse and inflow into the measuring space (first space 20) when the pumping voltage Vp0 is applied to the main pumping means 44.

In the interior of the first space 20, the partial pressure of oxygen is controlled so that NO in the atmosphere is not reduced by the inner pumping electrode 40, for example, the partial pressure of oxygen in which the reaction of NO→1/ $2N_2+1/2O_2$ is not caused even in an environment of being heated by the external measurement gas and being heated by the heater 80. That is, if NO contained in the measurement gas is reduced in the first space 20, it is impossible to correctly measure NOx in the second space 22 disposed downstream. In this meaning, it is preferable to establish a situation in which NO is not reduced by any component relevant to the reduction of NO (in this case, the metal component of the inner pumping electrode 40) in the first space 20. This is achieved by using a material having low reducibility with respect to NO, for example, an alloy of Au and Pt for the inner pumping electrode 40.

The measurement gas contained in the first space 20 is introduced into the second space 22 via the second diffusion rate-determining section 32. The measurement gas, which has been introduced into the second space 22, is finely adjusted so that the partial pressure of oxygen thereof has a constant and low value of partial pressure of oxygen in accordance with the pumping action for oxygen caused by the auxiliary control voltage Vp1 applied between the outer pumping electrode 42 and the auxiliary pumping electrode 60 of the auxiliary pumping means 62.

The second diffusion rate-determining section 32 functions to decrease the pumping current Ip1 flowing through the auxiliary pumping means 62 by limiting the amount of oxygen contained in the measurement gas to diffuse and flow into the measuring space (second space 22) when the auxiliary control voltage Vp1 is applied to the auxiliary pumping means 62.

In the second space 22, the partial pressure of oxygen is controlled so that NO in the atmosphere is not reduced by the auxiliary pumping electrode 60 in an environment of being heated by the external measurement gas and being heated by the heater 80, in the same manner as in the interior of the first space 20. Therefore, it is preferable to use a material having a weakened reducing ability or no reducing ability with respect to the NO component contained in the measurement gas, in the same manner as in the inner pumping electrode 40.

The measurement gas, which has the partial pressure of oxygen having been controlled in the second space 22 as described above, is introduced into the detecting electrode 70 via the third diffusion rate-determining section 72.

In the sensor element 12, the auxiliary pumping means 62 is provided for the second space 22 so that the partial pressure of oxygen in the internal atmosphere thereof always has a constant and low value of partial pressure of oxygen. Therefore, even when the partial pressure of oxygen in the atmosphere to be introduced from the first space 20 into the second space 22 is changed depending on the oxygen concentration of the measurement gas, the partial pressure of oxygen in the atmosphere in the second space 22 can always have a constant and low value owing to the pumping action of the auxiliary pumping means 62. As a result, it is possible to make the control to provide a low value of partial pressure of oxygen at which the measurement of NOx is not substantially affected.

NOx in the measurement gas having been introduced into the detecting electrode 70 is reduced or decomposed around the detecting electrode 70 to cause, for example, the reaction of NO→1/2N$_2$+1/2O$_2$. In this process, a predetermined voltage Vp2, for example, 400 mV is applied between the detecting electrode 70 and the reference electrode 48 of the measuring pumping means 74 so that the oxygen is pumped out from the second space 22 to the reference gas-introducing space 18.

Therefore, the pumping current Ip2 flowing through the measuring pumping means 74 has a value which is proportional to the oxygen concentration in the second space 22, i.e., the sum of the oxygen concentration in the second space 22 and the oxygen concentration produced by the reduction or decomposition of NOx effected by the detecting electrode 70.

In this process, the oxygen concentration in the second space 22 is controlled to be constant by the auxiliary pumping means 62. Therefore, the pumping current Ip2 flowing through the measuring pumping means 74 is proportional to the concentration of NOx. Further, the concentration of NOx corresponds to the amount of diffusion of NOx restricted by the third diffusion rate-determining section 72. Therefore, even when the oxygen concentration of the measurement gas is greatly changed, the concentration of NOx can be correctly measured by the measuring pumping means 74 with the ammeter.

According to this fact, almost all of the pumping current value Ip2, which is obtained with the measuring pumping means 74, represents the amount of reduction or decomposition of NOx. Therefore, the pumping current value Ip2 does not depend on the oxygen concentration in the measurement gas as well.

In the sensor element 12, the oxygen suddenly enters the sensor element 12 through the gas-introducing hole 28 as a result of the pulsation of the exhaust pressure in the exhaust tube or the like. However, the oxygen from the exhaust tube or the like does not enter the first space 20 directly, but the oxygen enters the buffering space 24 before the first space 20. In other words, the sudden change of the oxygen concentration caused by the pulsation of the exhaust pressure is counteracted by the buffering space 24. The influence of the pulsation of the exhaust pressure exerted on the first space 20 is substantially negligible.

As a result, the correlation is improved between the oxygen concentration in the measurement gas and the pumping amount of oxygen brought about by the main pumping means 44 in the first space 20. It is possible to improve the measurement accuracy in the measuring pumping means 74. Simultaneously, it is possible to use the first detecting means 50, for example, as a sensor for determining the air-fuel ratio as well.

In this procedure, lean and rich conditions of the air-fuel ratio can be detected by using the pumping current Ip0 of the main pumping means 44, and the stoichiometry of the air-fuel ratio can be detected by using the voltage V3 between the outer pumping electrode 42 and the reference electrode 48.

Further, the clogging-preventive space 26 is provided between the gas-introducing hole 28 and the fourth diffusion rate-determining section 34. Therefore, it is possible to avoid the clogging in the vicinity of the inlet of the buffering space 24, which would be otherwise caused by particulates (for example, soot and oil combustion waste) produced in the measurement gas in the exhaust tube or the like. Thus, it is possible to realize the highly accurate measurement of the NOx component performed by the measuring pumping means 74.

Figure 2:
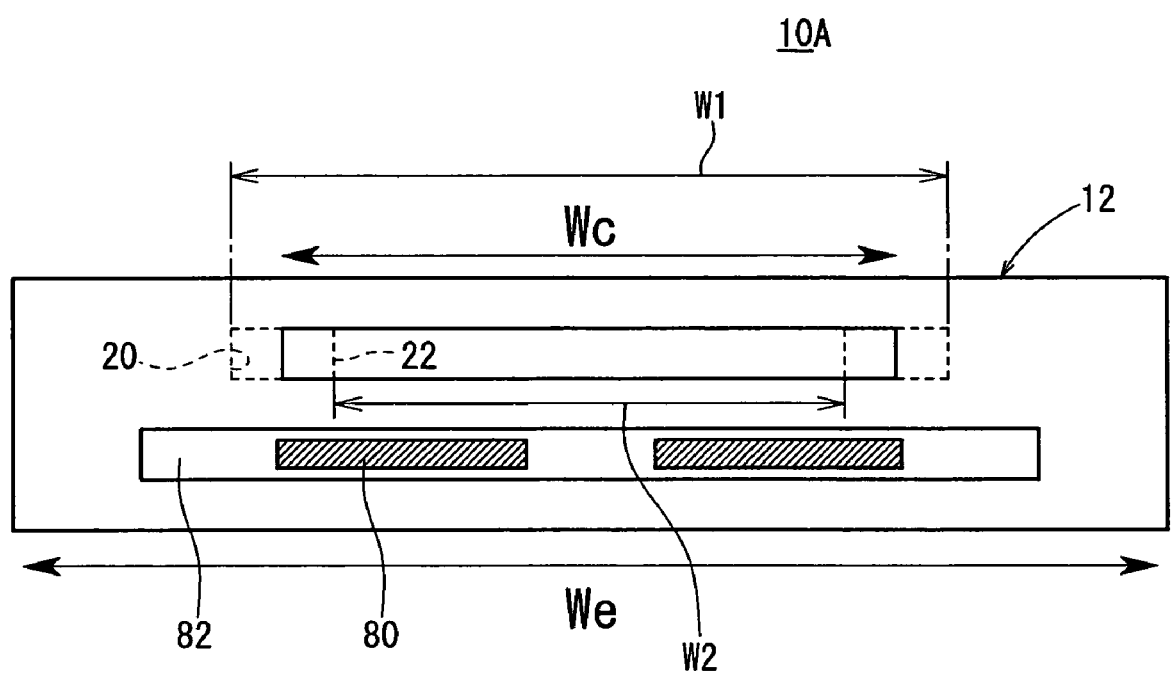
FIG. 2 illustrates a relationship between a width of a gas-introducing hole and a width of an end of a sensor element in the gas sensor according to the first embodiment.

As shown in FIG. 2, the gas sensor 10A according to the first embodiment is designed so that the following expression is satisfied:

$$0.3 \leq (Wc/We) < 0.7$$

provided that "We" represents the lateral width of the end of the sensor element 12 and "Wc" represents the lateral width of the gas-introducing hole 28, and the following expression is satisfied:

$$W2 < Wc < W1$$

provided that "W1" represents the width of the first space 20 and "W2" represents the width of the second space 22.

In general, in a gas sensor, the sensor element 12 is maintained at a predetermined temperature by using, for example, the heater 80 in order to improve the detection accuracy. When the measurement gas having an arbitrary temperature is introduced in this state, thermal stress by the temperature change is generated in the sensor element 12. In particular, because the space is formed in the vicinity of the gas-introducing hole 28, the mechanical strength is low and the stress is apt to be concentrated.

Therefore, for example, when sudden temperature change is caused, crack may appear around a base point or start point at which the stress is concentrated.

However, in the gas sensor 10A, the ratio (Wc/We) between the lateral width We of the end of the sensor element 12 and the lateral width Wc of the gas-introducing hole 28 is not less than 0.3 and less than 0.7. Accordingly, the mechanical strength is increased in the vicinity of the gas-introducing hole 28, and the thermal stress is reduced as well.

As a result, it is possible to decrease the stress generated in the sensor element 12, and it is possible to decrease the appearance of the crack or the like in the sensor element 12. This results in the improvement in reliability of the gas sensor 10A.

If the ratio (Wc/We) is too large, the mechanical strength may be lowered in the vicinity of the gas-introducing hole 28 and the crack tends to appear. On the other hand, if the ratio (Wc/We) is too small, an inconvenience arises such that the function of the gas sensor 10A is not fulfilled.

A first exemplary experiment will now be described. In the first exemplary experiment, the changes of thermal stress as time passes was measured at three points, i.e., Points P1, P2, and P3 for Comparative Example 1, Example 1, and Example 2 respectively. In this exemplary experiment, the measurement was performed in a calm or quiet state in which the flow rate was zero.

Figure 3:
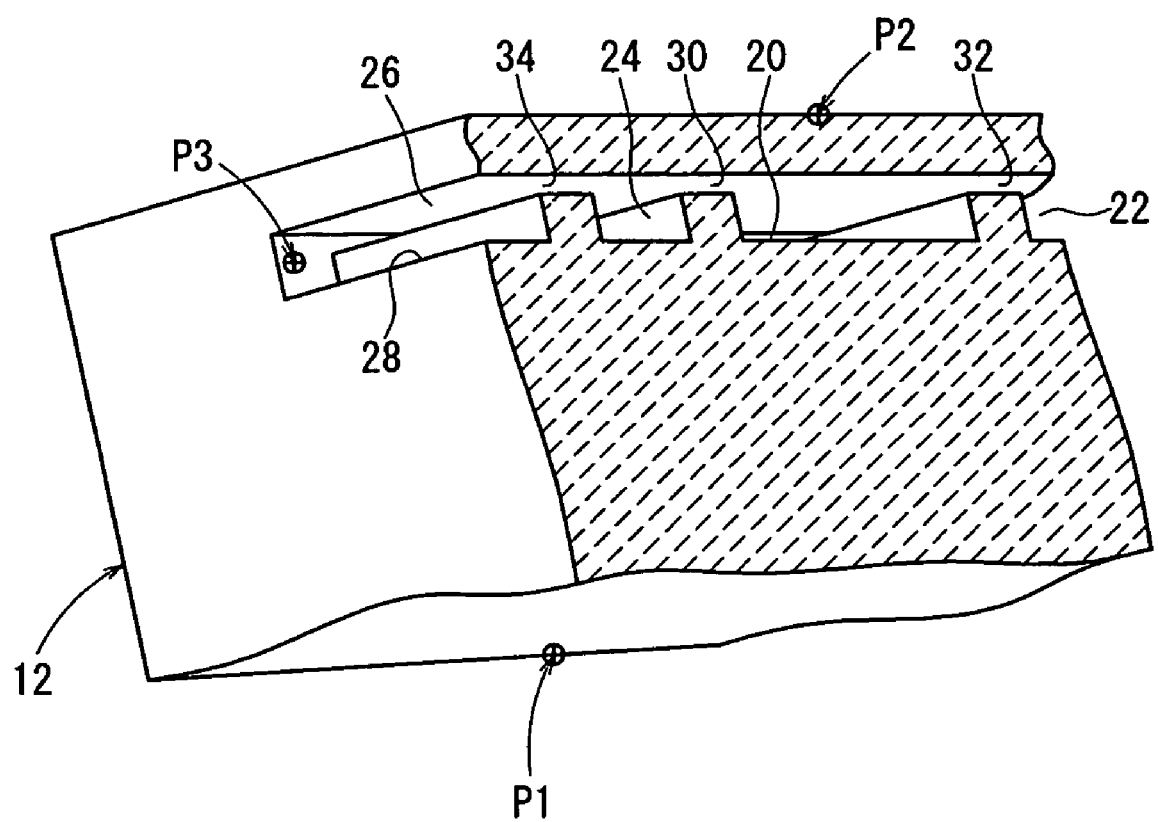
FIG. 3 illustrates three points for measuring the thermal stress of the gas sensor in illustrative experiments.

FIG. 3 schematically illustrates the specific places of the three points P1, P2, and P3. Point P1 was disposed at a position corresponding to the first space 20, which was located at a lower side end of the sensor element 12. Point P2 was disposed at a center of a portion corresponding to the first space 20, which was located at an upper portion of the sensor element 12. Point P3 was disposed at a side wall portion of the gas-introducing hole 28.

Figure 4:
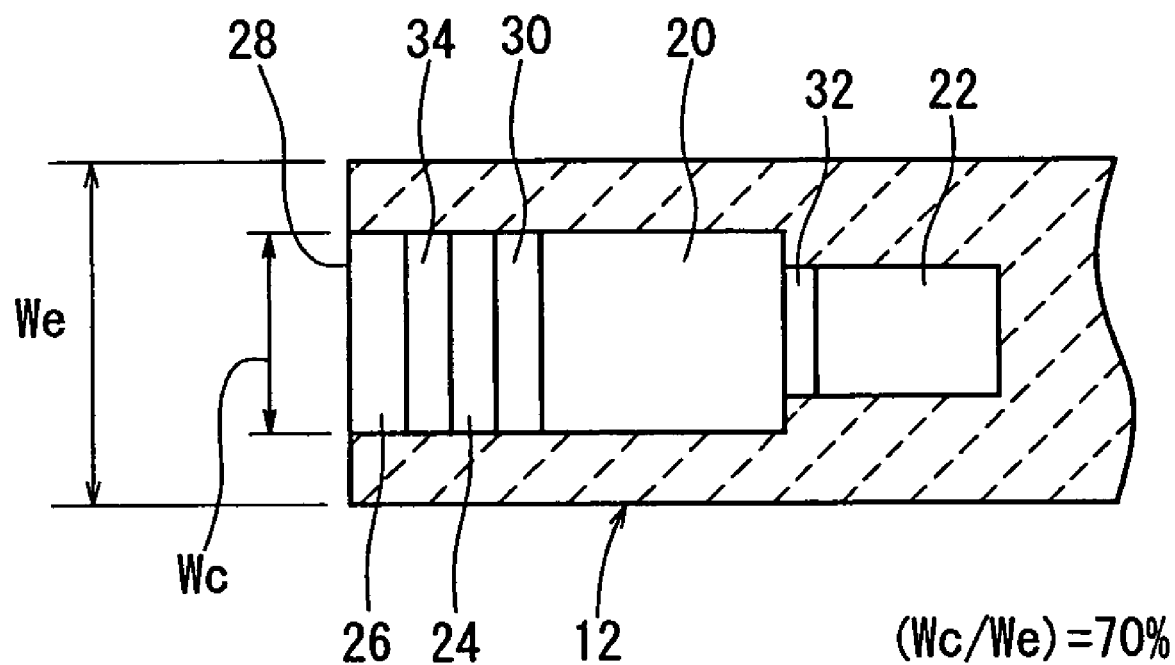
FIG. 4 is a lateral sectional view illustrating, with partial omission, an arrangement of Comparative Example 1 used in a first exemplary experiment.
Figure 5:
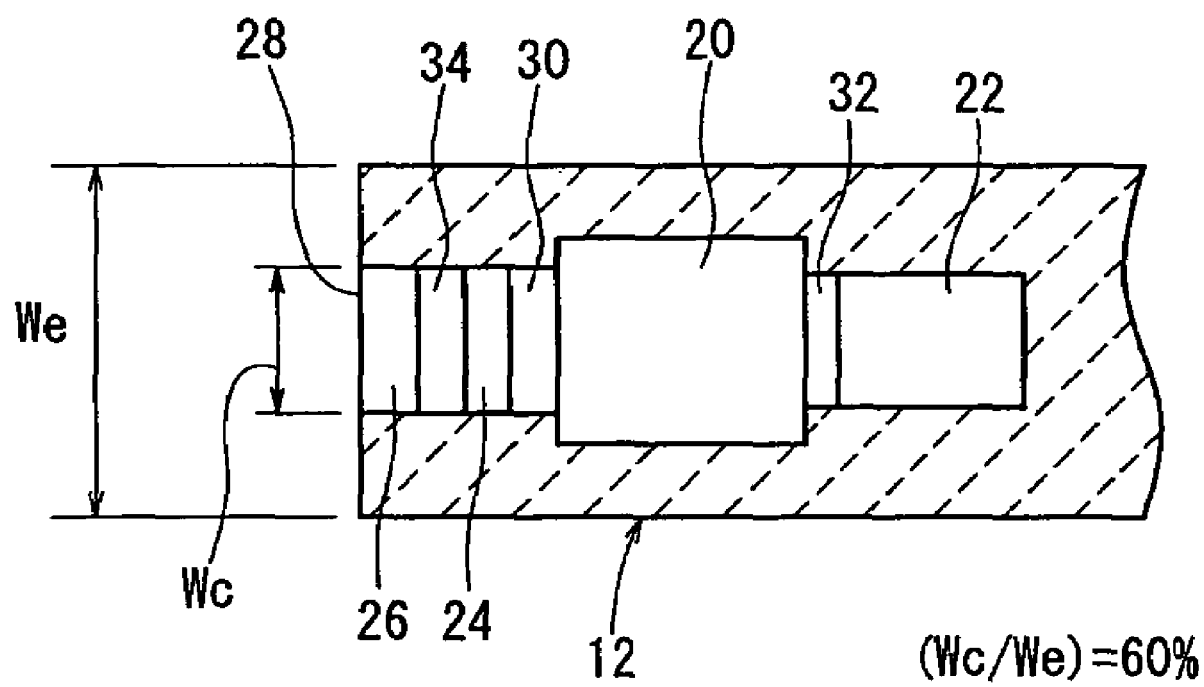
FIG. 5 is a lateral sectional view illustrating, with partial omission, an arrangement of Example 1 used in the first exemplary experiment.
Figure 6:
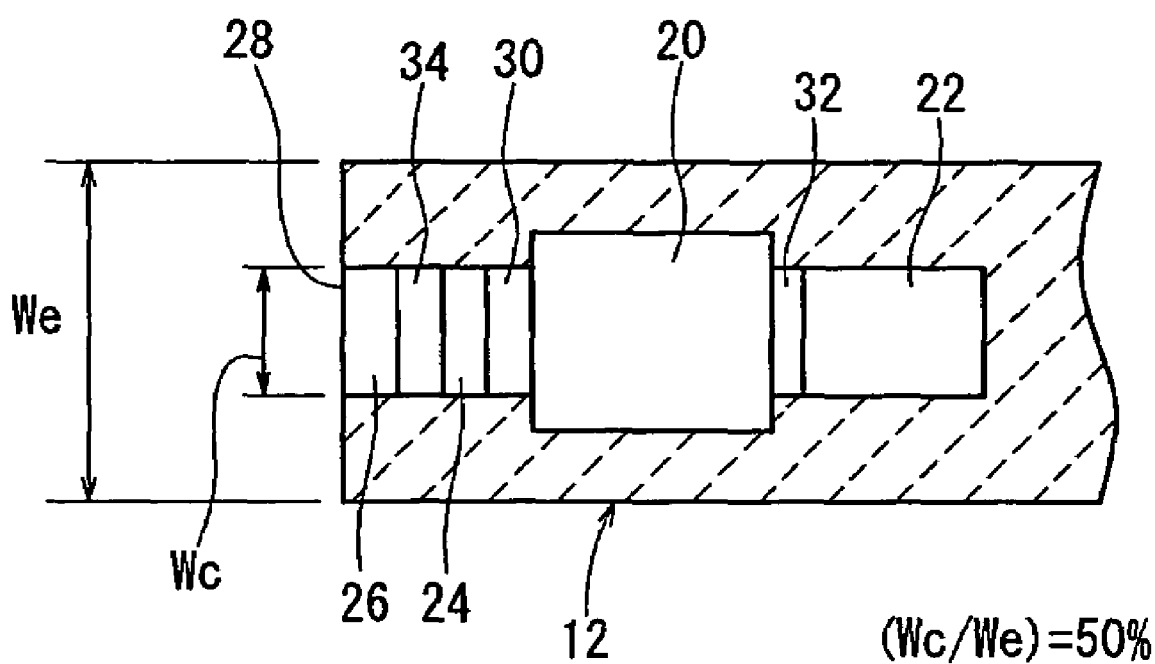
FIG. 6 is a lateral sectional view illustrating, with partial omission, an arrangement of Example 2 used in the first exemplary experiment.

As shown in FIG. 4, Comparative Example 1 was illustrative of a case in which the ratio (Wc/We) between the lateral width We of the end of the sensor element 12 and the lateral width Wc of the gas-introducing hole 28 was 0.7. As shown in FIG. 5, Example 1 was illustrative of a case in which the ratio (Wc/We) was 0.6. As shown in FIG. 6, Example 2 was illustrative of a case in which the ratio(Wc/We) was 0.5.

Figure 7:
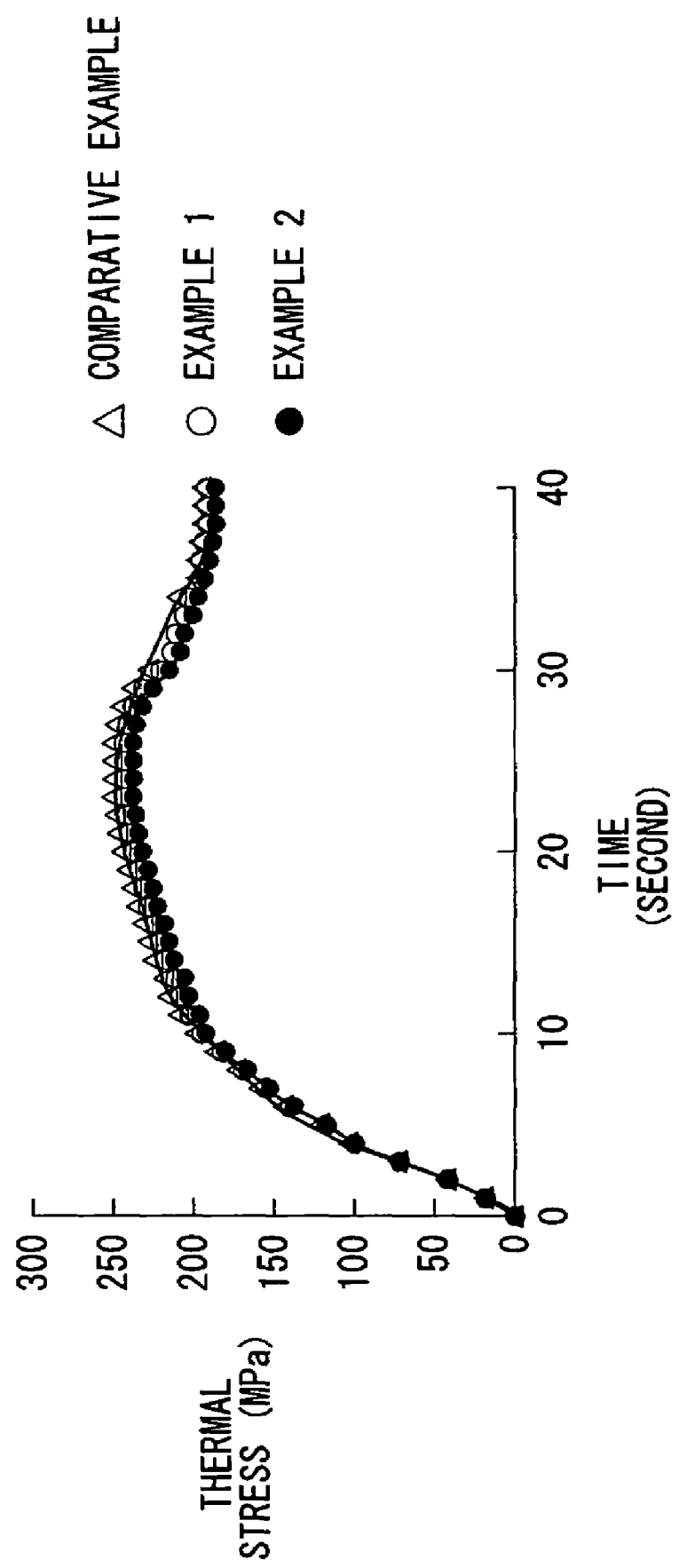
FIG. 7 shows changes of the thermal stress at Point P1 as time passes in Example 1 and Example 2.
Figure 8:
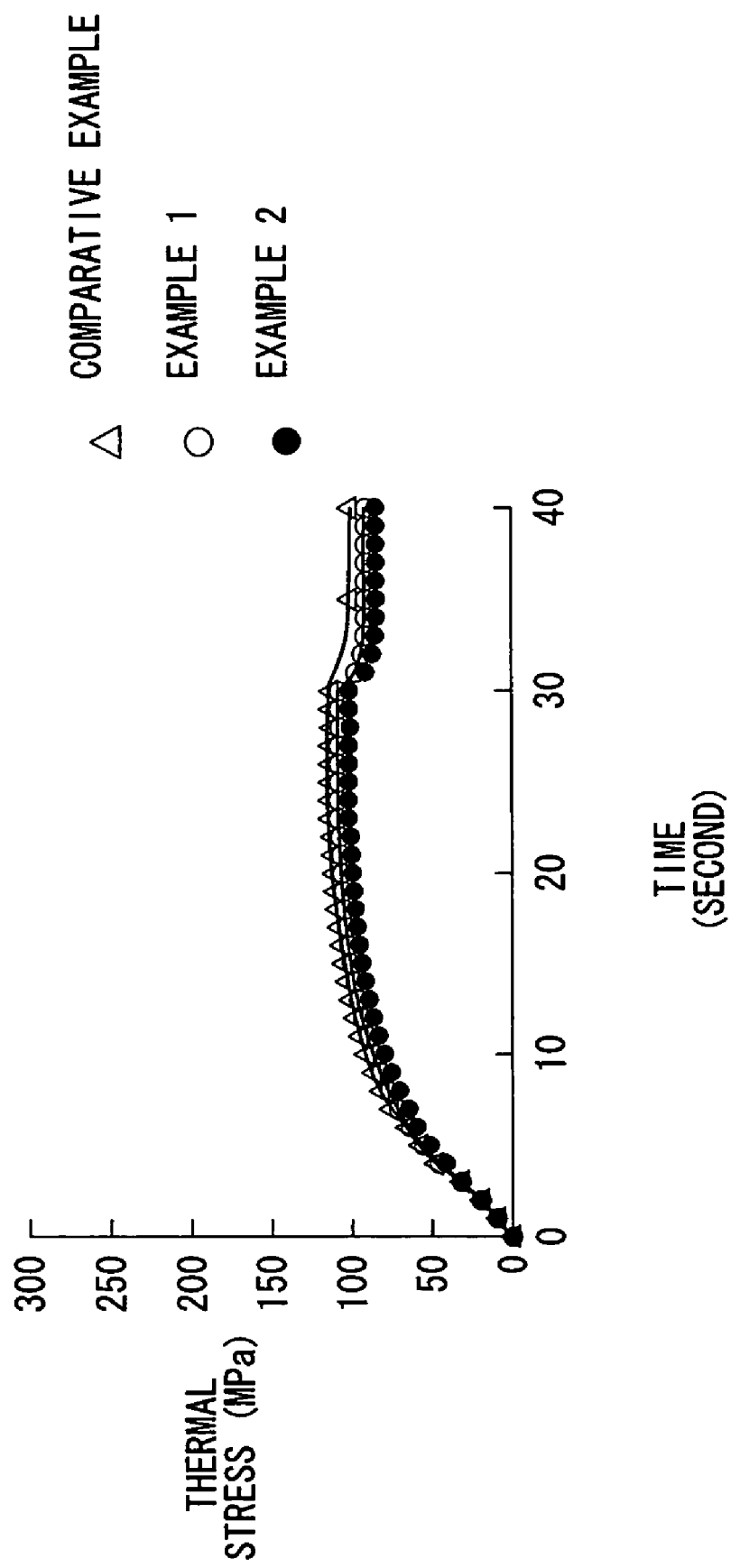
FIG. 8 shows changes of the thermal stress at Point P2 as time passes in Comparative Example 1, Example 1, and Example 2.
Figure 9:
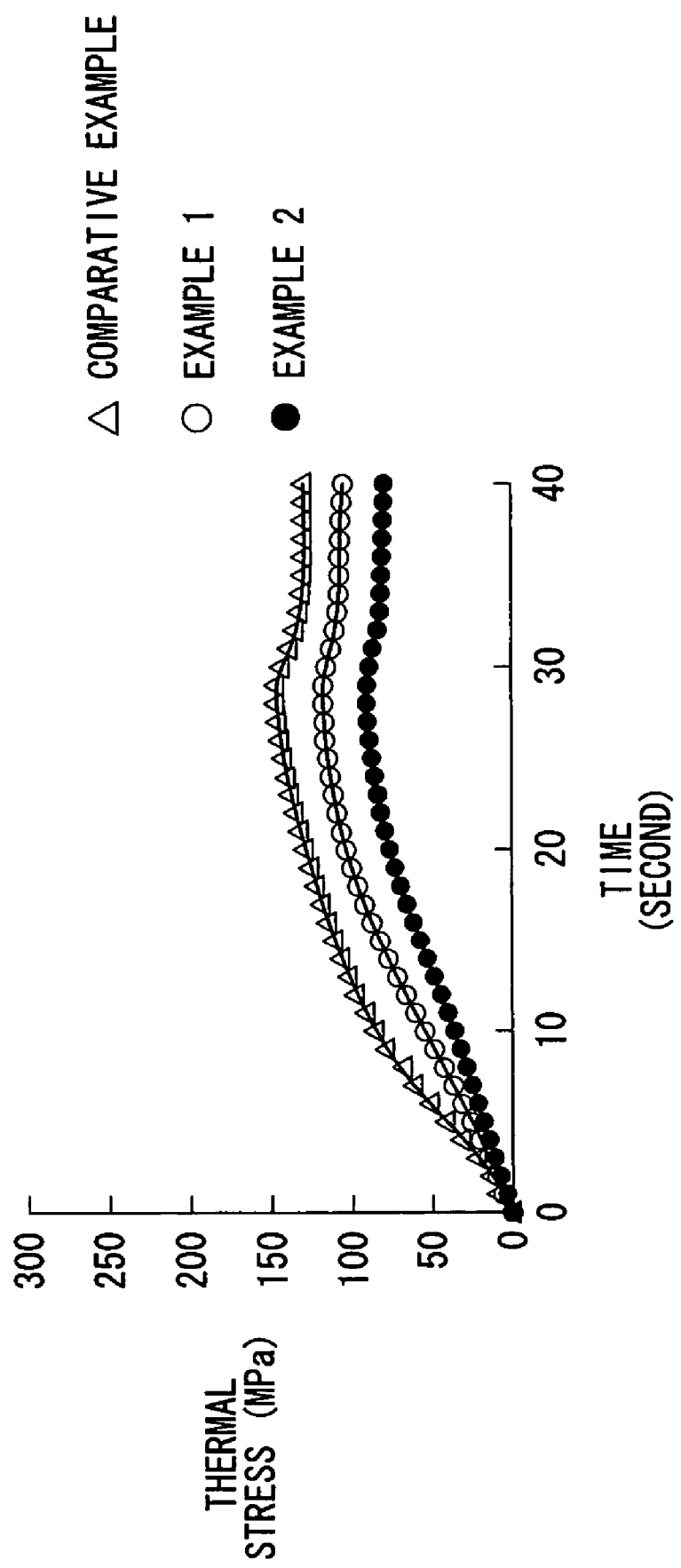
FIG. 9 shows changes of the thermal stress at Point P3 as time passes in Comparative Example 1, Example 1, and Example 2.

Results of the measurement are shown in FIGS. 7 to 9. FIGS. 7, 8, and 9 show the results of the measurement of the thermal stress changes as time passes at Point P1, Point P2, and Point P3, respectively. In FIGS. 7 to 9, a characteristic of Comparative Example 1 is depicted by plotting open triangles, a characteristic of Example 1 is depicted by plotting open circles, and a characteristic of Example 2 is depicted by plotting solid circles.

According to the results of the measurement, the thermal stress at Point P1 scarcely differed among Comparative Example 1, Example 1, and Example 2 as shown in FIG. 7. As shown in FIG. 8, the thermal stress at Point P2 was as follows. The thermal stress in Example 1 was slightly lower than that in Comparative Example 1. The thermal stress in Example 2 was slightly lower than that in Example 1. When the peak values were compared, 120 MPa was obtained for Comparative Example 1, 110 MPa was obtained for Example 1, and 100 MPa was obtained for Example 2.

The difference in thermal stress clearly appeared at Point P3. As shown in FIG. 9, in general, the thermal stress was low in Example 2, the thermal stress was low in Example 1 next to Example 2, and the thermal stress was highest in Comparative Example 1. When the peak values were compared, about 140 MPa was obtained for Comparative Example 1, about 120 MPa was obtained for Example 1, and about 90 MPa was obtained for Example 2. The peak value of Example 2 was lower than that of Comparative Example 1 by 50 MPa.

Next, several modified embodiments of the gas sensor 10A according to the first embodiment as described above will be explained with reference to FIGS. 10A to 12B.

Figure 10A:
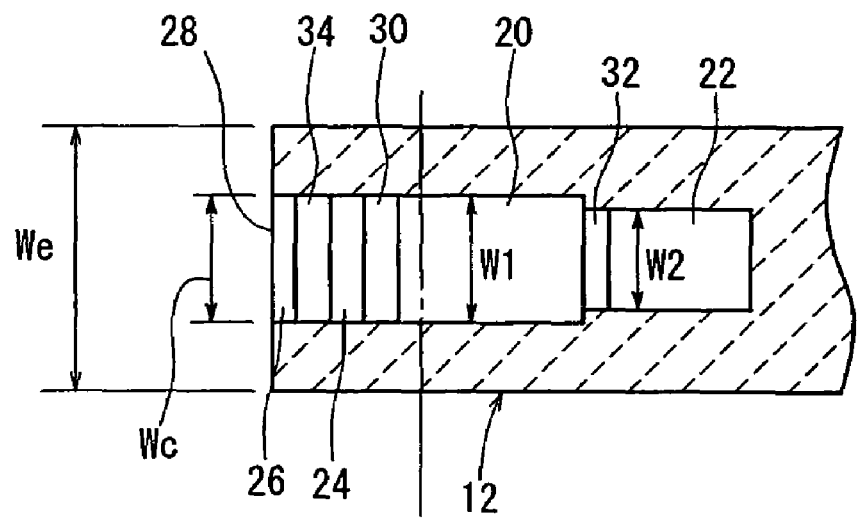
FIG. 10A is a lateral sectional view illustrating, with partial omission, a first modified embodiment of the gas sensor according to the first embodiment.
Figure 10B:
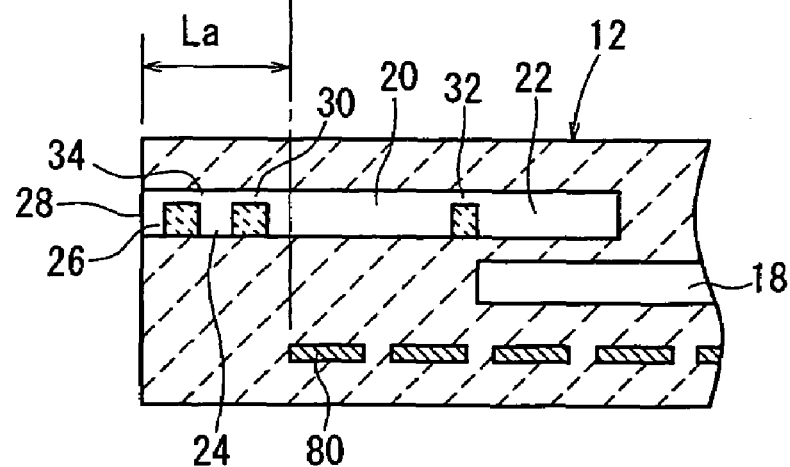
FIG. 10B is a longitudinal sectional view in relation to FIG. 10A.

First, as shown in FIGS. 10A and 10B, a gas sensor 10Aa according to a first modified embodiment is constructed in approximately the same manner as the gas sensor 10A according to the first embodiment described above. However, the gas sensor 10Aa is different from the gas sensor 10A in the following points.

That is, the ratio (Wc/We) between the lateral width We of the end of the sensor element 12 and the lateral width Wc of the gas-introducing hole 28 satisfies the following expression:

$$0.3 \leq (Wc/We) < 0.7$$

Moreover, the relationship among the lateral width Wc of the gas-introducing hole 28, the width W1 of the first space 20, and the width W2 of the second space 22 satisfies the following expression:

$$W2 < W1 = Wc$$

Further, the following expression is satisfied provided that La represents the distance from the projected position of the end of the heater 80 on the upper surface of the sensor element 12 to the end of the sensor element 12:

$$0.2 < (La/We) < 0.5$$

The projected position of the end of the heater 80 on the upper surface of the sensor element 12 is located and deviated away from the gas-introducing hole 28 as compared with the projected position of the starting end of the first space 20 on the upper surface of the sensor element 12.

Figure 11A:
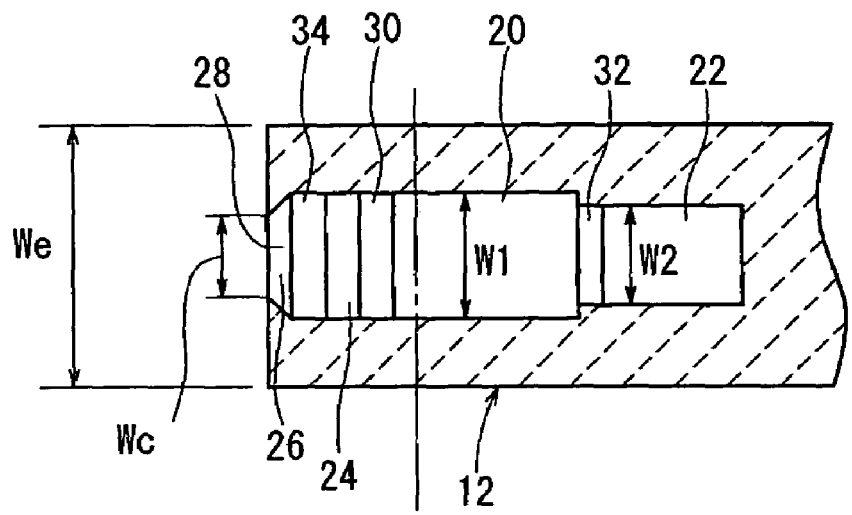
FIG. 11A is a lateral sectional view illustrating, with partial omission, a second modified embodiment of the gas sensor according to the first embodiment.
Figure 11B:
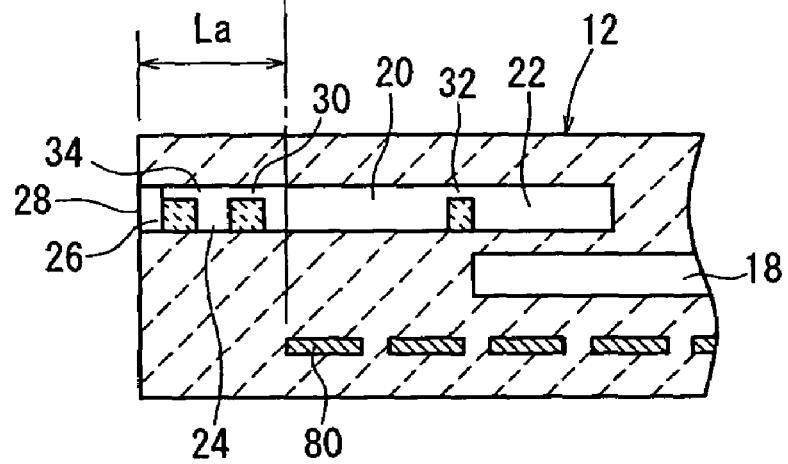
FIG. 11B is a longitudinal sectional view in relation to FIG. 11A.

Next, as shown in FIGS. 11A and 11B, a gas sensor 10Ab according to a second modified embodiment is constructed in approximately the same manner as the gas sensor 10Aa according to the first modified embodiment. However, the gas sensor 10Ab is different from the gas sensor 10Aa in the following points.

The ratio (Wc/We) between the lateral width We of the end of the sensor element 12 and the lateral width Wc of the gas-introducing hole 28 satisfies the following expression:

$$0.3 \leq (Wc/We) < 0.7$$

Moreover, the relationship among the lateral width Wc of the gas-introducing hole 28, the width W1 of the first space 20, and the width W2 of the second space 22 satisfies the following expression:

$$Wc < W2 < W1$$

Further, the following expression is satisfied by the distance La from the projected position of the end of the heater 80 on the upper surface of the sensor element 12 to the end of the sensor element 12:

$$0.2 < (La/We) < 0.5$$

The projected position of the end of the heater 80 on the upper surface of the sensor element 12 is located and deviated away from the gas-introducing hole 28 as compared with the projected position of the starting end of the first space 20 on the upper surface of the sensor element 12.

Figure 12A:
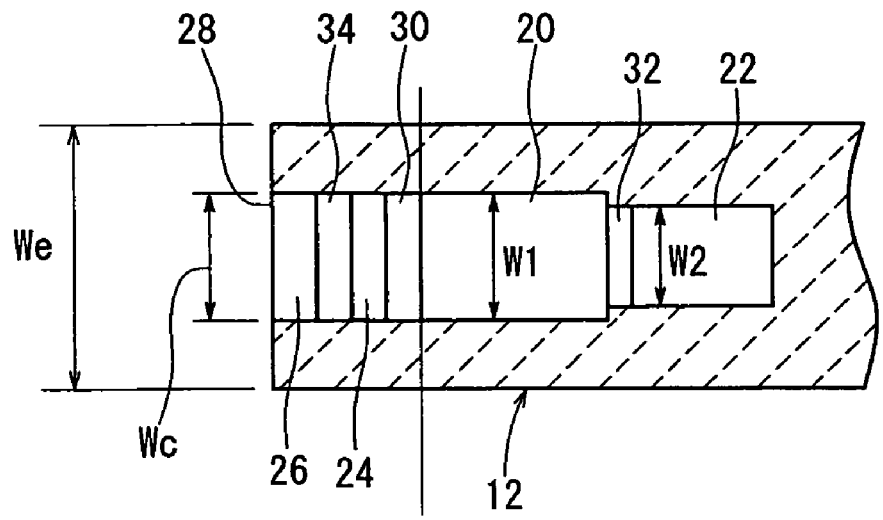
FIG. 12A is a lateral sectional view illustrating, with partial omission, a third modified embodiment of the gas sensor according to the first embodiment.
Figure 12B:
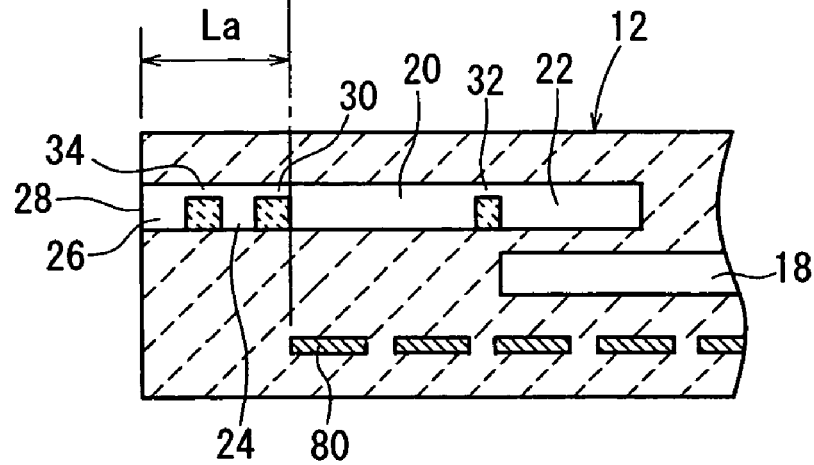
FIG. 12B is a longitudinal sectional view in relation to FIG. 12A.

Next, as shown in FIGS. 12A and 12B, a gas sensor 10Ac according to a third modified embodiment is constructed in approximately the same manner as the gas sensor 10Aa according to the first modified embodiment. However, the gas sensor 10Ac is different from the gas sensor 10Aa in the following points.

The ratio (Wc/We) between the lateral width We of the end of the sensor element 12 and the lateral width Wc of the gas-introducing hole 28 satisfies the following expression:

$$0.3 \leq (Wc/We) < 0.7$$

Moreover, the relationship among the lateral width Wc of the gas-introducing hole 28, the width W1 of the first space 20, and the width W2 of the second space 22 satisfies the following expression:

$$W2 < W1 = Wc$$

Further, the following expression is satisfied by the distance La from the projected position of the end of the heater 80 on the upper surface of the sensor element 12 to the end of the sensor element 12:

$$0.2 < (La/We) < 0.5$$

Furthermore, the projected position of the end of the heater 80 on the upper surface of the sensor element 12 is approximately coincident with the projected position of the starting end of the first space 20 on the upper surface of the sensor element 12.

It is possible to reduce the stress generated in the sensor element 12, and it is possible to decrease the occurrence of any crack or the like in the sensor element 12 in the gas sensors 10Aa to 10Ac according to the first to third modified embodiments as well.

In particular, in the gas sensors 10Aa to 10Ac according to the first to third modified embodiments, the ratio (La/We) between the distance La and the width We of the end of the sensor element 12 satisfies 0.2<La/We<0.5. Therefore, the heat generated by the heater 80 is hardly transmitted to the neighborhood of the gas-introducing hole 28, and the sudden temperature change, which would be otherwise caused by the introduction of the measurement gas, is scarcely caused. As a result, it is possible to further reduce the stress generated in the sensor element 12, and it is possible to further improve the reliability of the gas sensors 10Aa to 10Ac.

When the partial pressure of oxygen of the measurement gas introduced into the first space 20 is controlled at the predetermined value, the larger the volume of the first space 20 is, the more the efficiency is improved. The partial pressure of oxygen of the measurement gas having a large volume can be controlled at the predetermined value.

In view of the above, in order to increase the volume of the first space 20, it is firstly proposed that the width W1 of the first space 20 is increased. However, in this case, if the lateral width of the sensor element 12 is limited in order to miniaturize the gas sensor, the side wall sectioning the first space 20 has a low mechanical strength, and the crack may appear in the side wall.

On the other hand, it is also proposed that the length of the first space 20 is increased. However, the closer to the gas-introducing hole 28 the starting end of the first space 20 is, the lower the mechanical strength in the vicinity of the gas-introducing hole 28 is, and it may be impossible to reduce the stress in the vicinity of the gas-introducing hole 28.

However, in the case of the gas sensor 10Ac according to the third embodiment, the projected position of the end of the heater 80 on the upper surface of the sensor element 12 is approximately coincident with the projected position of the starting end of the first space 20 on the upper surface of the sensor element 12. Therefore, it is possible to reduce the stress in the vicinity of the gas-introducing hole 28, and it is possible to expand the volume of the first space 20 as well.

A second exemplary experiment will now be described. In the second exemplary experiment, the thermal stress changes as time passes was measured at the three points, i.e., Points P1, P2, and P3 (see FIG. 3) for Comparative Example 2, Example 3, Example 4, and Example 5, respectively. The experimental conditions were the same as those in the first exemplary experiment described above.

Figure 13A:
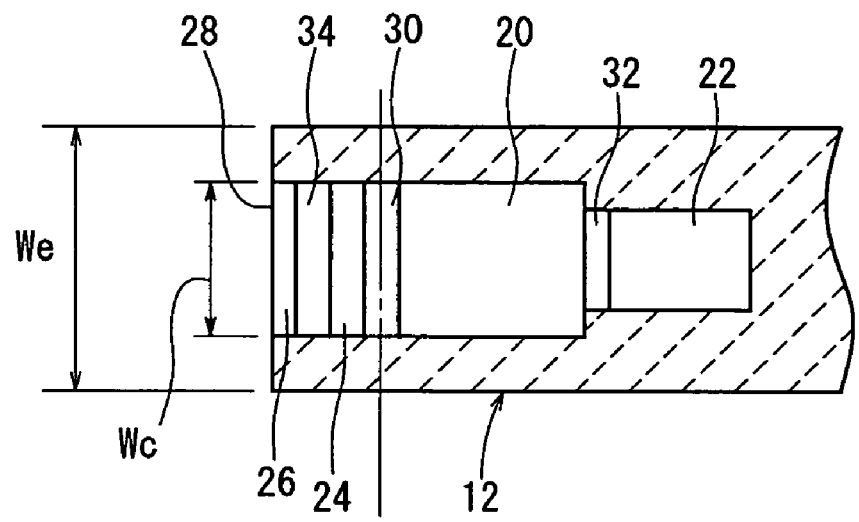
FIG. 13A is a lateral sectional view illustrating, with partial omission, Comparative Example 2 used in a second exemplary experiment.
Figure 13B:
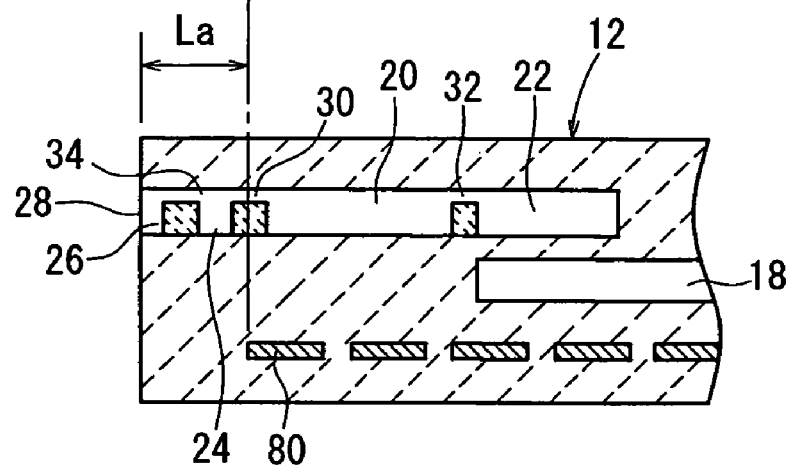
FIG. 13B is a longitudinal sectional view in relation to FIG. 13A.

As shown in FIGS. 13A and 13B, Comparative Example 2 was illustrative of a case in which the ratio (Wc/We) between the lateral width We of the end of the sensor element 12 and the lateral width Wc of the gas-introducing hole 28 was 0.7, and the ratio (La/We) between the distance La from the projected position of the end of the heater 80 on the upper surface of the sensor element 12 to the end of the sensor element 12 and the width We of the sensor element 12 was 0.2.

Example 3 was constructed in the same manner as the gas sensor 10Aa according to the first modified embodiment described above, Example 4 was constructed in the same manner as the gas sensor 10Ab according to the second modified embodiment described above, and Example 5 was constructed in the same manner as the gas sensor 10Ac according to the third modified embodiment described above.

Figure 16:
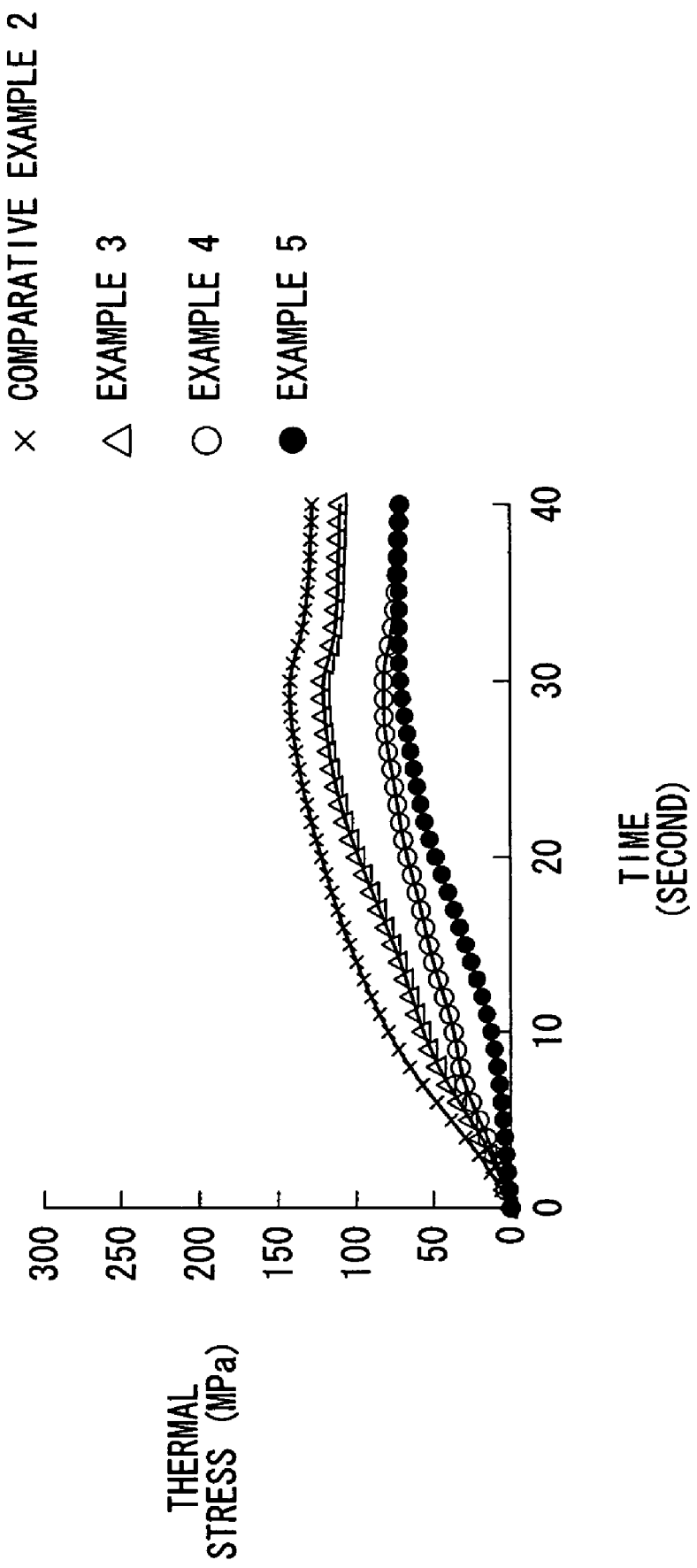
FIG. 16 shows changes of the thermal stress at Point P3 as time passes in Comparative Example 2 and Examples 3 to 5.
Figure 17:
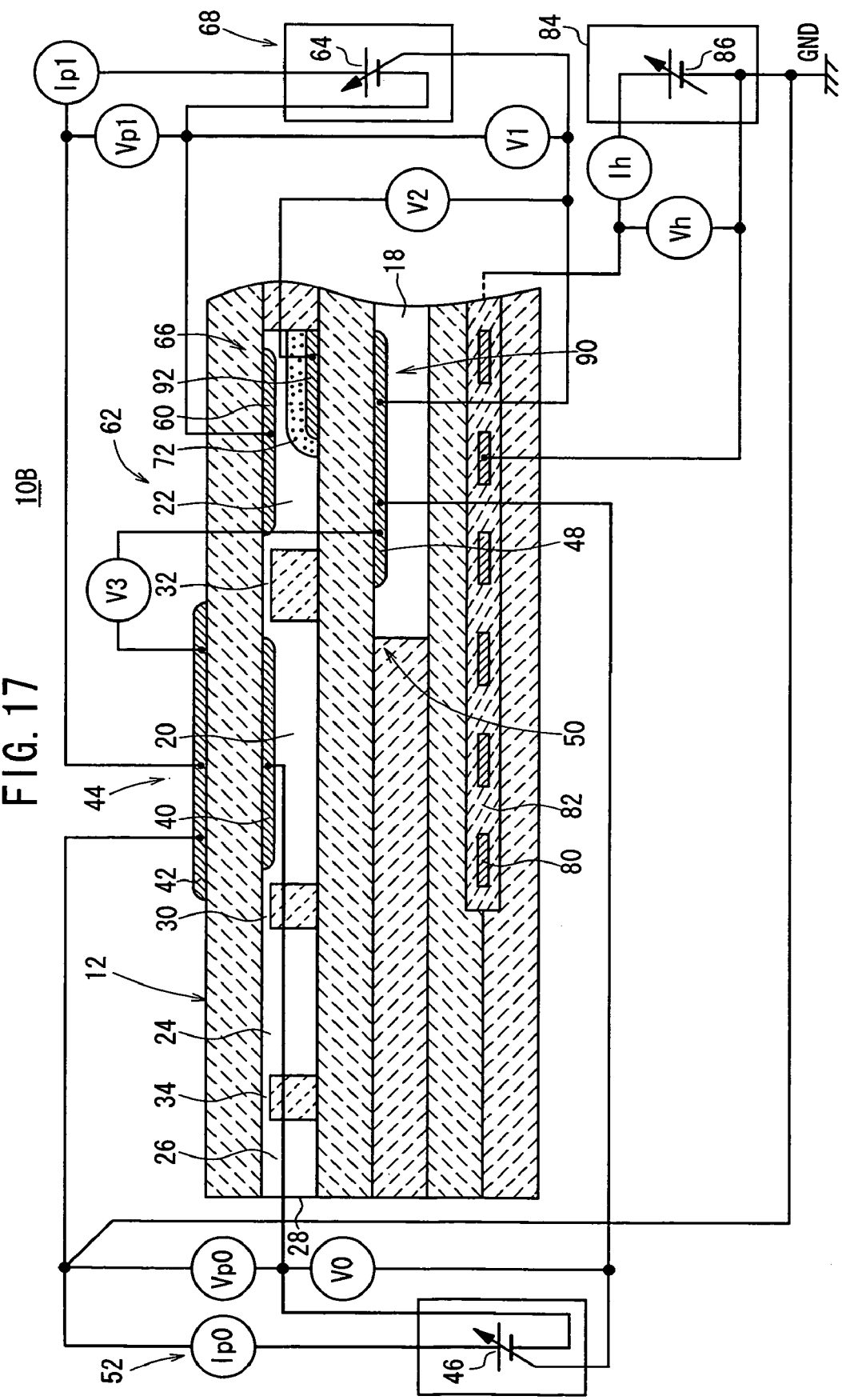
FIG. 17 shows a cross-sectional arrangement illustrating a gas sensor according to a second embodiment.

Results of the measurement are shown in FIGS. 14 to 16. FIGS. 14, 15, and 16 show the results of the measurement of the thermal stress changes as time passes at Point P1, Point P2, and Point P3, respectively. In FIGS. 14, 15, and 16, a characteristic of Comparative Example 2 is depicted by plotting crosses, a characteristic of Example 3 is depicted by plotting open triangles, a characteristic of Example 4 is depicted by plotting open circles, and a characteristic of Example 5 is depicted by plotting solid circles.

According to the results of the measurement, as for the thermal stress at Point Pi, Examples 3 to 5 were generally lower than Comparative Example 2, and Examples 3 to 5 were hardly different from each other as shown in FIG. 14. As shown in FIG. 15, the thermal stress at Point P2 was similar to the above. That is, Examples 3 to 5 were generally lower than Comparative Example 2, and Examples 3 to 5 were hardly different from each other.

At Point P3, as shown in FIG. 16, Examples 3 to 5 were generally lower than Comparative Example 2 in the same manner as in the results obtained at Points P1 and P2. However, the difference clearly appeared among Examples 3 to 5. That is, observing only Examples 3 to 5, in general, Example 5 was lowest, Example 4 was low next to Example 5, and Example 3 was highest.

According to the second exemplary experiment described above, it is appreciated that the gas sensor 10Ac according to the third modified embodiment constructed in the same manner as Example 5 has the structure which most hardly suffers the thermal stress.

In the gas sensor 10A according to the first embodiment described above (including the various modified embodiments 10Aa, 10Ab, and 10Ac), the measuring pumping means 74 is used to detect the NOx concentration. However, a third detecting means 90 may be used as in a gas sensor 10B according to a second embodiment shown in FIG. 17.

The third detecting means 90 includes a detecting electrode 92, the reference electrode 48 formed in the reference gas-introducing space 18, and the solid electrolyte layer interposed between the electrodes 92, 48. In this arrangement, an electromotive force (electromotive force of an oxygen concentration cell) V2, which corresponds to the difference in oxygen concentration between the atmosphere around the detecting electrode 92 and the atmosphere around the reference electrode 48, is generated between the detecting electrode 92 and the reference electrode 48 of the third detecting means 90.

Therefore, when the electromotive force (voltage) V2 generated between the detecting electrode 92 and the reference electrode 48 is measured by using a voltmeter, the partial pressure of oxygen in the atmosphere around the detecting electrode 92 (in other words, the partial pressure of oxygen defined by the oxygen produced by the reduction or decomposition of the measurement gas component (NOx)) is detected as the voltage value V2. The degree of the change of the electromotive force V2 represents the concentration of NOx.

It is a matter of course that the gas sensor according to the present invention is not limited to the embodiments described above, which may be embodied in other various forms without deviating from the gist or essential characteristics of the present invention.

What is claimed is:

1. A gas sensor comprising a sensor element having a gas-introducing hole at an end of said sensor element, and having upper and lower surfaces;

said sensor element including a reference gas-introducing space, a clogging preventative space, a buffering space, a first space for introducing a measurement gas thereinto from said gas-introducing hole via the clogging preventative space, the buffering space and a first diffusion rate-determining section, a main pumping means for controlling a partial pressure of oxygen contained in said measurement gas introduced into said first space to be substantially constant, a second space for introducing said measurement gas thereinto from said first space via a second diffusion rate-determining section, an electric signal-generating converting means for reducing or decomposing a NOx component contained in said measurement gas introduced from said second space via a third diffusion rate-determining section to generate an electric signal corresponding to an amount of oxygen produced thereby so that a concentration of NOx existing in said measurement gas is determined from said electric signal, a first detecting means including an inner electrode in said first space and a reference electrode in said reference gas-introducing space, and a heater for maintaining at least said first space and said second space at a predetermined temperature, said heater being disposed only at a lower potion of said sensor element, wherein $$0.3 \leq (Wc/We) < 0.7$$

wherein We represents a lateral width of said end of said sensor element, and Wc represents a lateral width of said gas-introducing hole, and $$0.2 < (La/We) < 0.5$$

wherein La represents a distance from a projected position of an end of said heater on said upper surface of said sensor element to said end of said sensor element, wherein a starting end position is defined as a projected position of an end of said first space close to said gas-introducing hole on said upper surface of said sensor element, and said projected position of said end of said heater on said upper surface of said sensor element extends to said starting end position, and wherein an air-fuel ratio of said measurement gas is determined by said first detecting means from a voltage between said inner electrode and said reference electrode and a pumping current of said main pumping means.

2. The gas sensor according to claim 1, wherein said electric signal-generating converting means is a measuring pumping means which reduces or decomposes said NOx component contained in said measurement gas introduced from said second space via said third diffusion rate-determining section, which pumps out oxygen produced thereby, and which detects a current generated by pumping out the oxygen.

3. The gas sensor according to claim 1, wherein said electric signal-generating converting means is a detecting means which reduces or decomposes said NOx component contained in said measurement gas introduced from said second space via said third diffusion rate-determining section and which detects an electromotive force corresponding to a difference between an amount of oxygen produced by said reduction or decomposition and an amount of oxygen contained in a reference gas.

4. The gas sensor according to claim 1, wherein each of said first diffusion rate-determining section and said second diffusion rate-determining section is defined by a slit provided in said sensor element.

5. The gas sensor according to claim 1, wherein said sensor element further includes a fourth diffusion rate-determining section between said clogging preventative space and said buffering space.

6. The gas sensor according to claim 5, wherein said fourth diffusion rate-determining section is defined by a slit provided in said sensor element.

7. The gas sensor according to claim 6, wherein a lateral width of said clogging-preventive space, a lateral width of said buffering space, a lateral width of said slit of said first diffusion rate-determining section, and a lateral width of said slit of said fourth diffusion rate-determining section are substantially identical with each other.

8. The gas sensor according to claim 7, wherein said lateral width of said gas-introducing hole is substantially identical with said lateral width of said clogging-preventive space.

9. The gas sensor according to claim 1, further comprising an auxiliary pumping means for controlling a partial pressure of oxygen contained in said measurement gas introduced into said second space.

* * * * *